US009884715B2

(12) United States Patent
Hoofman et al.

(10) Patent No.: US 9,884,715 B2
(45) Date of Patent: Feb. 6, 2018

(54) FOOD PACKAGE WITH INTEGRATED RFID-TAG AND SENSOR

(75) Inventors: Romano Hoofman, Geel (BE); Roel Daamen, Herkenbosch (NL); Youri Victorovitch Ponomarev, Leuven (BE); Fotopoulou Kyriaki, Brussels (BE); Matthias Merz, Leuven (BE); Gilberto Curatola, Korbek-lo (BE); Anton Tombeur, Lommel (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 13/116,920

(22) Filed: May 26, 2011

(65) Prior Publication Data

US 2011/0291806 A1 Dec. 1, 2011

(30) Foreign Application Priority Data

May 31, 2010 (EP) .................................... 10164438

(51) Int. Cl.
*H04Q 5/22* (2006.01)
*B65D 79/02* (2006.01)
(Continued)

(52) U.S. Cl.
CPC .......... *B65D 79/02* (2013.01); *G01N 33/0062* (2013.01); *B65D 2203/10* (2013.01); *G01N 33/02* (2013.01)

(58) Field of Classification Search
None
See application file for complete search history.

(56) References Cited

U.S. PATENT DOCUMENTS 6,538,569 B1 *  3/2003  Dunn ........................... 340/540
7,254,883 B2    8/2007  Schmid et al.
(Continued)

FOREIGN PATENT DOCUMENTS

DE    10 2004 019 427 A1    11/2005
DE    10 2004 040 831 A1    3/2006
(Continued)

OTHER PUBLICATIONS

Wang, N. et al. "Wireless Sensors in Agriculture and Food Industry—Recent Developments and Future Perspective", Computers and Electronics in Agriculture, vol. 50, pp. 1-14 (2006).
(Continued)

*Primary Examiner* — Brian Zimmerman
*Assistant Examiner* — Kevin Lau

(57) ABSTRACT

A container for containing a perishable substance has a container wall with an inner side and an outer side. The wall has an electrically conductive layer extending between the inner side and the outer side. The inner side faces the space containing the substance. The container comprises electronic circuitry having a sensor for sensing a physical property or condition of the substance, and an antenna for communicating an RF signal to a receiver, external to the container. The RF signal is indicative of the physical property or condition sensed. The sensor is positioned so as to be exposed to the space containing the substance in operational use of the container. The antenna is positioned at the outer side, or between the outer side and the electrically conductive layer, and is electrically isolated from the electrically conductive layer.

17 Claims, 2 Drawing Sheets

(51) Int. Cl.
*G01N 33/00* (2006.01)
*G01N 33/02* (2006.01)

(56) References Cited

U.S. PATENT DOCUMENTS

| | | | |
|---|---|---|---|
| 8,035,524 B2 | 10/2011 | Sakama et al. | |
| 2004/0018326 A1* | 1/2004 | Kasahara | B32B 27/10 428/34.3 |
| 2004/0049428 A1* | 3/2004 | Soehnlen et al. | 705/25 |
| 2005/0027330 A1* | 2/2005 | Govari | 607/60 |
| 2005/0280542 A1* | 12/2005 | Shieh | 340/572.8 |
| 2006/0139200 A1 | 6/2006 | Jensen | |
| 2006/0220856 A1* | 10/2006 | Shaffer et al. | 340/572.1 |
| 2007/0176773 A1 | 8/2007 | Smolander et al. | |
| 2007/0258048 A1* | 11/2007 | Pitchers | 353/26 R |
| 2007/0273507 A1* | 11/2007 | Burchell et al. | 340/539.27 |
| 2008/0191961 A1* | 8/2008 | Tuttle | 343/893 |
| 2008/0231438 A1* | 9/2008 | Curcio | 340/539.13 |
| 2008/0272131 A1* | 11/2008 | Roberts et al. | 220/592.25 |
| 2009/0085750 A1 | 4/2009 | Waldner et al. | |
| 2010/0052215 A1* | 3/2010 | Emond et al. | 264/275 |
| 2010/0219252 A1 | 9/2010 | Kikuchi et al. | |
| 2010/0271208 A1* | 10/2010 | Steinmetz et al. | 340/572.1 |
| 2011/0037568 A1* | 2/2011 | Kim et al. | 340/10.1 |

FOREIGN PATENT DOCUMENTS

| | | |
|---|---|---|
| EP | 1 375 131 A1 | 1/2004 |
| JP | 4-502816 A | 5/1992 |
| JP | 2004-075155 A | 3/2004 |
| JP | 2007-261664 A | 10/2007 |
| JP | 2008-542142 A | 11/2008 |
| JP | 2009 093318 A | 4/2009 |
| WO | 03/044521 A1 | 5/2003 |

OTHER PUBLICATIONS

"The Truly Integrated Circuit is Printed and Flexible", Printed Electronics World, 4 pgs, retrieved from the Internet at: http://www.printedelectronicsworld.com/articles/the_truly_integrated_circuit_is_printed_and_flexible_00002136.asp, (Mar. 24, 2010).

Extended European Search Report for European Patent Application No. 10164438.3 (Nov. 29, 2010).

Office Action for foreign counterpart Japanese Patent Application No. 2011-120970 (dated Dec. 4, 2012).

* cited by examiner

FOOD PACKAGE WITH INTEGRATED RFID-TAG AND SENSOR

CROSS-REFERENCE TO RELATED APPLICATIONS

This application claims the priority under 35 U.S.C. § 119 of European patent application no. 10164438.3, filed on May 31, 2010, the contents of which are incorporated by reference herein.

FIELD OF THE INVENTION

The invention relates to a container configured for containing a substance and comprising electronic circuitry for sensing a physical property of the substance and providing a wireless signal indicative of the physical property sensed.

BACKGROUND OF THE INVENTION

Radio-frequency identification (RFID) tags have been widely used to identify and track objects. An RFID tag is attached to, or incorporated in, a physical object and has an antenna for communicating with a remote receiver through RF (radio-frequency electromagnetic waves). The RFID tag may communicate a unique identifier, representative of the RFID tag and, therefore, of the individual physical object. The RFID tag may be a passive RFID tag that generates power for its operation upon receipt of an incident electromagnetic wave generated by an external source and of a proper frequency corresponding to the sensitivity of the antenna. Alternatively, the RFID tag may be an active RFID tag, accommodating its own power supply, e.g., a battery or an energy scavenger, for autonomous operation.

An RFID tag can be combined with a sensor so as to implement a low-cost remote sensor for use in telemetry applications. For example, the Wireless Identification and Sensing Platform (WISP) is a type of passive RFID tag that is configured for supporting sensing, e.g., of temperature or of acceleration, for local processing of a sensor signal, and for communicating the processed signal via RF to an external receiver.

RFID technology is helping to transform logistics by providing a means of tracking and tracing individual products throughout the supply chain. Nowadays, increasingly more e research and development is ongoing in the integration of active RFID tags with sensors that monitor the quality of the product. In recent years, wireless sensors have been adopted in food processing to monitor and control the quality attributes of food products. For example, a temperature sensor can be inserted into a food item for recording the temperature over time, and for transmitting the temperature data wirelessly to a central controller.

RFID tagging has been accepted as a new technology for a well-structured traceability system on data collecting, and human, animal and product tracking. It has been projected that the applications of RFID will grow rapidly in the next 10 years with a compound annual revenue growth rate (2003-2010) of 32.2% see, e.g., N. Wang et al., Computers and Electronics in Agriculture 50 (2006), pp. 1-14.

SUMMARY OF THE INVENTION

The operation of the combination of an RFID tag and a sensor requires that the antenna of the RFID tag be positioned such the antenna is enabled to transmit an RF signal to an external receiver and, in case of a passive RFID tag, to also receive an RF signal from an external transmitter. That is, the use of an RFID tag in the vicinity of an electrically conductive object may hamper the operation of the RFID tag as the RF signals may get shielded by the electrically conductive object, depending on the frequency of the RF signals and the properties of the electrically conductive object.

Consider a container or food package that is configured for containing a perishable substance, e.g., a food substance such as a dairy product, a fruit juice, or another perishable product such as a medicine, etc. Well-known examples of such containers are manufactured by Tetra Pak. Typically, such a container is designed for aseptic packaging of the substance and has a laminated container wall that comprises an electrically conductive layer, e.g., aluminum. The aluminum layer is used to prevent the substance from being exposed to light and to oxygen.

Accordingly, the presence of the electrically conductive layer in the container wall presents a problem to using a conventional combination of an RFID tag integrated with a sensor. Also note that, conventionally, an RFID chip is directly bonded on a substrate carrying the (planar) antenna. That is, the RFID chip and the antenna are co-planar in that they are accommodated on the same substrate, thus forming a single unit.

The inventors therefore propose a container with a space for containing a substance and a container wall determining the space. The container wall has an inner side and an outer side. The container wall has an electrically conductive layer extending between the inner side and the outer side. That is, the electrically conductive layer is arranged substantially in parallel with the inner side and the outer side. The inner side faces the space containing the substance in operational use of the container. The container comprises electronic circuitry having a sensor for sensing a physical property, or a physical condition, of the substance in operational use of the container. The electronic circuitry also has an antenna for communicating a radio-frequency signal to a receiver, external to the container. The radio-frequency signal is indicative of the physical property or condition sensed in operational use of the container. The sensor is positioned so as to be exposed to the space containing the substance in operational use of the container. The antenna is electrically isolated from the electrically conductive layer. The antenna is positioned at the outer side, or between the outer side and the electrically conductive layer.

In the invention, the sensor and the antenna are accommodated in different planes running parallel to the container wall. Accordingly, the sensor is positioned so as to be exposed to the substance, or to one or more chemical products released by the substance when the substance ages, or to the temperature or pressure to which the substance is subjected within the container. The antenna, on the other hand, is positioned on or near the outside of the container, away from, and electrically isolated from, the electrically conductive layer so as to be able to transmit the RF signal to an external receiver remote from the container.

The electronic circuitry may comprise signal processing circuitry to process the sensor signal received from the sensor. For example, the sensor is activated periodically or at any desired moment, and the sensor signal is logged in an onboard solid-state memory so as to compile a history file representative of, e.g., the aging of the substance. Alternatively, the sensor is activated periodically or at any desired moment, and the sensor signal is compared with a predetermined threshold in order to determine the end of the shelf-life of the substance. For example, the electronic circuitry is powered by an onboard power supply, e.g., a battery. The electronic circuitry may then have a timer that controls the moments of activating the sensor and registering the sensor signal. Alternatively, the electronic circuitry receives a first control signal from a source external to the container and via the antenna, in order to activate the sensor. The electronic circuitry may receive via the antenna a second control signal that causes the electronic circuitry to start transmitting via the antenna an RF signal, which carries the information about the logged history. Alternatively, when the signal processing circuitry has determined that the threshold has been reached, the electronic circuitry periodically transmits via the antenna an RF signal to an external receiver and indicative of the threshold having been reached.

The invention as specified above relates to commercially exploiting the invention in the embodiment of the container. The invention can also be commercially exploited as a laminate suitable for producing the container. For example, the invention also relates to a laminate for use in a container wall of a container, designed for containing a perishable substance. The laminate has a first side and a second side. The laminate has an electrically conductive layer extending between the first side and the second side. The first side is configured for facing a space containing the substance in operational use of the container. The laminate comprises electronic circuitry having a sensor for sensing a physical property or condition of the substance in operational use of the container, and also having an antenna for communicating a radio-frequency signal to a receiver, external to the container. The radio-frequency signal is indicative of the physical property or condition sensed in operational use of the container. The sensor is positioned at, or near, the first side so as to be exposed to the space containing the substance in operational use of the container. The antenna is positioned at the second side, or between the second side and the electrically conductive layer. The antenna is electrically isolated from the electrically conductive layer.

That is, pieces of such a laminate may be manufactured by a first party and provided to a second party, at whose premises the laminate is cut and folded to produce a container according to the invention, and filled with the substance. The electronic circuitry may be manufactured by the first party using printing electronics technology. For printing electronics see, e.g., "The truly integrated circuit is printed and flexible", Dr. Peter Harrop, Printed Electronics WORLD, Mar. 24, 2010, or the relevant entry in Wikipedia.

In an embodiment, the laminate comprises a battery for powering the electronic circuitry. The battery is provided so as to be physically isolated from the space for comprising the substance so as to prevent contamination of the substance by the battery in operational use of the container.

For completeness, reference is made to US patent application publication 2007/0176773, incorporated herein by reference. US patent application publication 2007/0176773 discloses a remotely readable sensor for indicating a usability condition of perishable products such as foodstuffs and medical drugs. The sensor incorporates a resistive element, whose resistance is responsive to the condition of the perishable product. According to the invention, the sensor is placed inside the foodstuff package. The element of the sensor forms a current loop with a first coil that is inductively coupled to a second coil of a remote reader device. The resistance of the element determines the quality factor of the resonant circuit formed by the element and the coil. Measuring the quality factor therefore enables to determine the resistance of the element and, therefore, the condition of the perishable product. US patent application publication 2007/0176773 neither discloses nor suggests the presence of an electrically conductive layer in the wrapping of foodstuff. The only example given of foodstuff-wrapping is a layer of HDPE (high-density polyethylene), which is an insulator.

BRIEF DESCRIPTION OF THE DRAWINGS

The invention is explained in further detail, by way of example and with reference to the accompanying drawing, wherein.

Throughout the Figures, similar or corresponding features are indicated by same reference numerals.

DETAILED DESCRIPTION OF EMBODIMENTS

Figure 1:
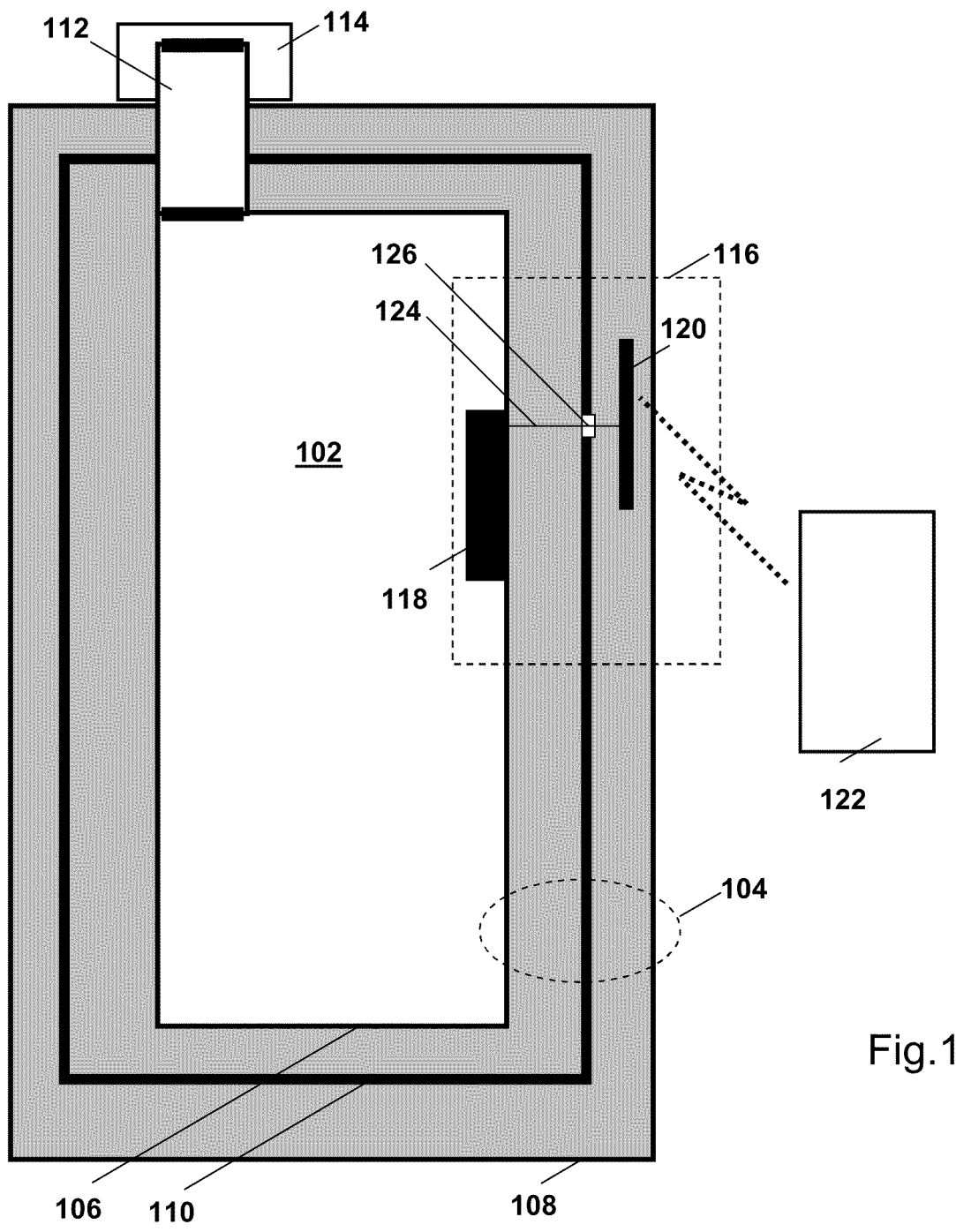
FIG. 1 is a block diagram of a container in the invention.

FIG. 1 is a block diagram of a container 100 in the invention. The container 100 has a space 102 for containing a perishable substance (not shown), e.g., fruit juice, and a layered container wall 104 that determines the space 102. The container wall 104 has an inner side 106 and an outer side 108. The container wall 104 has an electrically conductive layer 110 extending between the inner side 106 and the outer side 108. The inner side 106 faces the space 102 containing the substance in operational use of the container 100. The container 100 also comprises a spout 112 that is closed with a cap 114. Removing the cap 114 from the spout 112 enables a user to pour the fruit juice from the container 100 into, e.g., a tumbler (not shown) or a cup (not shown). The removable cap 114 closes the spout 112 for, e.g., transport of the container and keeping more oxygen from entering the container 100. The container 100 comprises electronic circuitry 116 having a sensor 118 for sensing a physical property of the substance in operational use of the container 100, and an antenna 120 for communicating a radio-frequency signal to a receiver 122, external to the container 100. The radio-frequency signal is indicative of the physical property sensed. The physical quantity comprises, for example, a temperature of the substance, or a change in temperature of the substance, a pressure in the space 102 or a change in pressure in the space 102, an acidity of the substance, a basicity of the substance, a concentration of a specific chemical compound released by the substance, etc. The sensor 118 is positioned at the inner side 106 of the container wall 104 so as to be exposed to the space 102 containing the substance in operational use of the container 100. For example, the sensor 118 is mounted on the inner side 106 of the container wall 104. Alternatively, the sensor 118 is recessed into the container wall 104 and exposed to the space 102 through an opening (not shown) in the inner side 106 of the container wall 104, or further recessed into the container wall 104 and exposed to the space 102 through openings (not shown) in both the inner side 106 of the container wall 104 and in the electrically conductive layer 110, etc. The antenna 120 is positioned at or near the outer side 108 of the container wall 104. That is, the antenna 120 is positioned on the outer side 108 or within the container wall 104 between the outer side 108 and the electrically conductive layer 110. The antenna 120 is electrically isolated from the electrically conductive layer 110.

The antenna 120 is functionally coupled with the sensor 118. For example, the configuration of the RFID sensor disclosed in US patent application publication 2007/0176773 could in principle be used if the antenna and sensor, electrically interconnected, were positioned at different sides of the electrically conductive layer 110 and electrically isolated from the electrically conductive layer 110. In another embodiment, the sensor 118 is functionally coupled to the antenna 120 via signal processing circuitry (not shown). The signal processing circuitry receives the sensor signal from the sensor 118. The signal processing circuitry then stores in an onboard memory (not shown) data, which is representative of the sensor signal received, for later retrieval by the receiver 122 via the antenna 120. For example, the onboard memory stores a batch of data, each individual one of the data being representative of an individual sensor signal captured at an individual moment. Alternatively, the signal processing circuitry receives the sensor signal from the sensor 118 and converts the sensor signal into a driving signal for driving the antenna 120 so as to transmit the RF signal to the receiver 122.

The sensor 118 and/or the signal processing circuitry may have an onboard power supply, e.g., a battery for powering the sensor 118 and/or the signal processing circuitry. The sensor 118 and/or the signal processing circuitry may then also have an onboard timer for determining when to activate the sensor 118 for supplying the sensor signal and/or for determining when to transmit the RF signal to the receiver 122. In the latter case, the combination of the sensor 118 and the antenna 120 is configured and functions as an active RFID tag. Alternatively, the sensor 118 and/or the signal processing circuitry are powered via an RF signal transmitted by an external source (not shown) and being of the proper frequency and incident on the antenna 120. In this case, the combination of the sensor 118 and the antenna 120 is configured and functions as a passive RFID tag.

The sensor 118, or at least the part of the sensor 118 that is exposed to the space 102, is implemented so as to prevent chemical or physical contamination of the substance in the space 102 by the exposed part of the sensor 118. The materials of the sensor 118 and the configuration of the sensor 118 are chosen in dependence on what physical quantity to sense and, possibly, on the chemical and/or physical properties of the substance. For example, if the sensor 118 comprises a temperature sensing device, the sensor 118 or the exposed part thereof may be covered by a protective film of a suitable material that is chemically inert with respect to the substance and that has a suitable thermal conductivity. Similarly, if the sensor 118 is configured for sensing a pressure, the exposed part of the sensor 118 may be covered by a protective film of a suitable material that is chemically inert with respect to the substance and that does not substantially interfere with sensing the pressure in the space 102. Accordingly, the temperature sensing device or the pressure sensing device on the one hand, and the substance on the other hand, interact only via the protective film. As another example, consider the sensor 118 comprising another device for sensing the presence or concentration of a chemical compound in the space 102 through a chemical reaction between the chemical compound and the materials of this other device. Then, neither the materials of this other device, nor the products of the chemical reaction should noticeably contaminate the substance.

If the sensor 118 is mounted on a substrate (not shown), similar considerations apply with regard to contamination of the substance as a result of part of the substrate being exposed to the space 102. If the sensor 118 and/or the signal processing circuitry have their own power supply, e.g., a battery, then similar considerations apply with regard to contamination of the substance as a result of part of the battery being exposed to the space 102.

The diagram of the container in FIG. 1 illustrates a first one of multiple options for positioning the sensor 118 and the antenna 120 at the container 100. In the first option, the sensor 118, or the substrate accommodating the sensor 118 and, optionally, the signal processing circuitry, is mounted on the inside 106 of the container wall 104. The sensor 118 and/or the signal processing circuitry are/is connected to the antenna 120 via an electrically conductive connection 124. The electrically conductive connection 124 penetrates the electrically conductive layer 110 via a passage 126. The electrically conductive connection 124 is electrically insulated from the electrically conductive layer 110. For example, an electrically insulating outer layer is provided around the electrically conductive connection 124. Alternatively, the container wall 104 is composed of a laminate of electrically insulating materials, apart from the electrically conductive layer 110. Then, the space in the passage 126 around the electrically conductive connection 124 is filled with an electrically insulating material so as to prevent a galvanic contact between the electrically conductive connection 124 and the electrically conductive layer 110.

Figure 2:
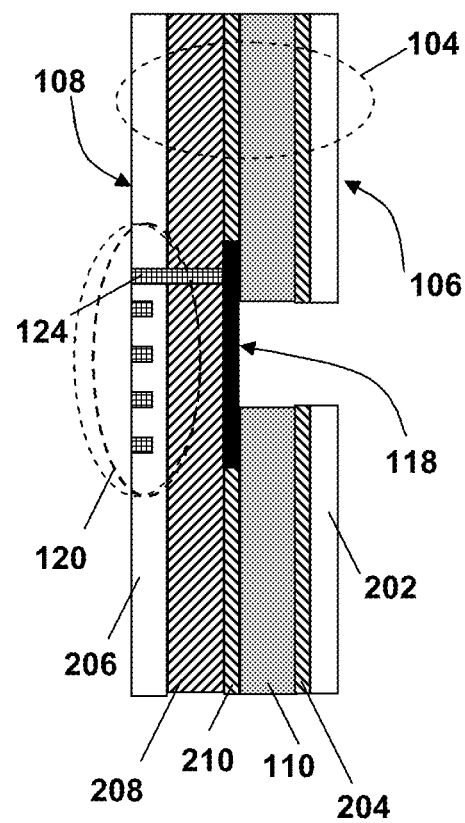
FIGS. 2 and 3 are diagrams of some details illustrating alternative configurations of a container in the invention.
Figure 3:
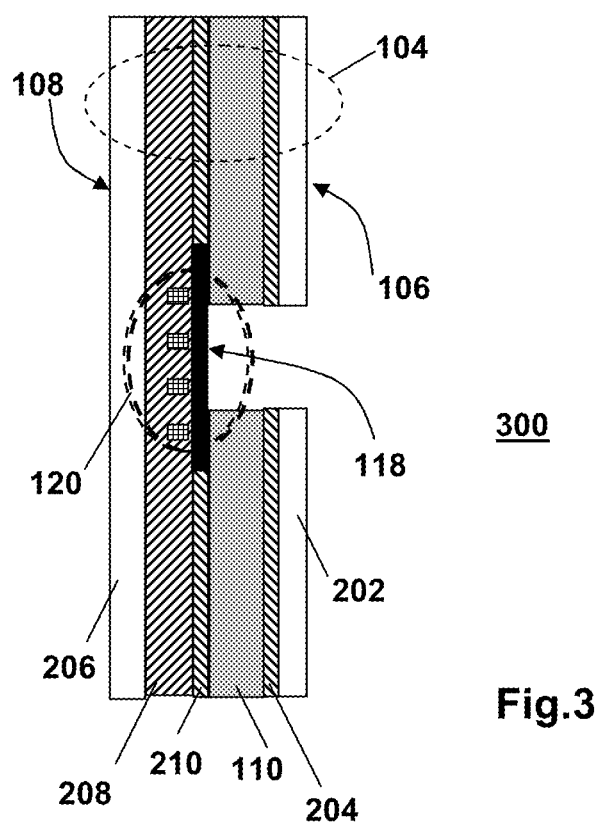

FIGS. 2 and 3 are diagrams of a second option 200 and a third option 300, respectively, for positioning the sensor 118 and the antenna 120.

In both the second option 200 and the third option 300, the container wall 104 is represented as a laminate, as mentioned above. Typically, the inner side 106 of the container wall 104 comprises a first layer 202 of metallocene polyethylene (mPE) for sealing in the fruit juice in the space 102. A second layer 204 of modified low-density polyethylene (LDPE) is positioned between the first layer 202 and the electrically conductive layer 110. The second layer 204 serves as an adhesion layer. The outer side 108 comprises a third layer 206 of LDPE as a protection against moisture from outside the container 100. Next to the third layer 206 is a fourth layer 208 of paper for providing mechanical stability and strength. Between the fourth layer 208 and the electrically conductive layer 110 is located a fifth layer 210 of LDPE.

The sensor 118 and, optionally, the signal processing circuitry are accommodated in or on the fifth layer 210, e.g., printed on the fifth layer 210 (LDPE) using printing electronics technology. Optionally, the signal processing circuitry and/or the battery is likewise accommodated in/on the fifth layer 210 using, e.g., printed electronics technology. The sensor 118 is exposed to the space 102 via respective holes in the electrically conductive layer 210, the second layer 204 and the first layer 202. Preferably the holes are aligned.

In the second option 200, the antenna 120 has a planar configuration and is accommodated on the outer side 108 in the third layer 206. The antenna 120 may be implemented using printed electronics technology. The antenna 120 is connected to the sensor 118, or to the signal processing circuitry, by means of the electrically conductive connection 124 that runs through the fourth layer 208 and the third layer 206. For example, corresponding holes are made in the fourth layer 208 and in the third layer 206 and filled with an electrically conductive paste.

Alternatively, the sensor 118 and, optionally, the signal processing circuitry and/or the battery, are accommodated in, or on, the fourth layer 208, e.g., printed on the fourth layer 208 (paper) using printing electronics technology. The fifth layer 210 is then also provided with a hole so as to have the sensor 118 exposed to the space 102.

In the third option 300, the antenna 120 has a planar configuration and is accommodated on the substrate that accommodates the sensor 118. The antenna 120 may be implemented using printed electronics technology. Optionally, the signal processing circuitry and/or the battery are accommodated on the same substrate using printed electronics technology. In the example shown in FIG. 3, the sensor 118 and, optionally the signal processing circuitry and the battery, are accommodated in or on the fifth layer 210.

Alternatively, the sensor 118 and, optionally, the signal processing circuitry and/or the battery, are accommodated in, or on, the fourth layer 208, e.g., printed on the fourth layer 208 (paper) using printing electronics technology. The fifth layer 210 is then also provided with a hole so as to have the sensor 118 exposed to the space 102.

The diagrams of FIGS. 1, 2 and 3 illustrate the invention as applied to, e.g., a milk carton or a carton for holding fruit juice. The invention can similarly be applied to other types of containers that are entirely made of an electrically conductive material, e.g., a stainless steel beer barrel (also referred to as cask or keg) or an aluminum drum, for containing a perishable substance, e.g., foodstuff or beverage. That is, the invention can also be applied to RFID tags combined with sensors for condition-monitoring of a substance contained in a container of an electrically conductive material. The invention can also be applied to a metallic food container such as a dish or a tray of aluminum foil. The circuitry of the RFID tag, e.g., the sensor 118 and/or the signal processing circuitry and/or the battery, is spatially separated from the antenna 120. The antenna is then accommodated on the outside of the container and electrically insulated from the container, and the circuitry of the RFID tag is accommodated on the inside of the container. The antenna and the circuitry of the RFID tag are galvanically connected via a hole in the wall of the container.

The invention claimed is:

1. An apparatus comprising:
a container with a space for containing a perishable substance and a laminated container wall determining the space, wherein the laminated container wall has an inner side, an outer side, and an electrically conductive layer extending between and substantially parallel with the inner side and the outer side wherein the inner side faces the space containing the substance in operational use of the container; and
electronic circuitry having:
a sensor circuit configured and arranged to sense a physical property or condition of the substance in operational use of the container; and
an antenna having a planar configuration, wherein the sensor circuit is arranged on a first substrate and the antenna is arranged on a second substrate, wherein the first and second substrates are arranged substantially parallel with respect to one another and along the laminated container wall and in different planes running along the inner and outer sides of the laminated container wall,
the sensor circuit being configured and arranged to
compare a value associated with the sensed physical property or condition of the substance to a predetermined threshold value, and
in response to the comparison of the value with the predetermined threshold value, drive the antenna to communicate a radio-frequency signal to a receiver, external to the container, with varying values over time based upon the comparison of the physical property or condition of the substance to the predetermined threshold value, in operational use of the container, the radio-frequency signal including data specifying the value of the physical property or condition sensed;
the electronic circuitry being configured and arranged with the container such that:
the sensor circuit is positioned so as to be exposed to the space containing the substance in operational use of the container;
the antenna is positioned between the outer side and the electrically conductive layer on a substrate that accommodates the sensor; and
the antenna is electrically isolated from the electrically conductive layer;
wherein the inner side of the laminated container wall comprises:
a first layer configured and arranged to seal the substance in the inner side of the container;
a second layer arranged between the first layer and the electrically conductive layer and configured and arranged to adhere the first layer to the electrically conducting layer; and
wherein the outside side of the laminated container wall comprises:
a third layer configured and arranged to protect against elements from outside the container;
a fourth layer configured and arranged to provide mechanical strength, the fourth layer including the sensor circuit printed thereon, the antenna being connected to the sensor circuit via an electrically conductive connection that runs through the fourth layer, the fourth layer defining a hole filled with an electrically conductive material via which the conductive connection runs; and
a fifth layer arranged between the fourth layer and the electrically conductive layer, the first layer, second layer, the electrically conductive layer, and the fifth layer are configured and arranged to define another hole that exposes the sensor to the space.

2. An apparatus for use in a container wall of a container designed for containing a perishable substance, the apparatus comprising:
a laminated container wall having:
a first side, a second side, and an electrically conductive layer extending between the first side and the second side, the first side, second side and electrically conductive layers being substantially parallel, wherein:
the first side is configured to face a space containing the substance in operational use of the container, the first side including a first layer configured and arranged to seal the substance inside the container and a second layer arranged between the first layer and the electrically conductive layer and configured and arranged to adhere the first layer to the electrically conducting layer,
the second side includes a third layer configured and arranged to protect against elements from outside the container, a fourth layer configured and arranged to provide mechanical strength, and a fifth layer arranged between the fourth layer and the electrically conductive layer, and
the electrically conductive layer is configured and arranged to at least partially surround the space and reduce exposure to light or oxygen in the space;
an electrically conductive connection that penetrates the electrically conductive layer via a passage, wherein the electrically conductive connection is electrically insulated from the electrically conductive layer of the laminated container wall; and
electronic circuitry within fourth layer in the laminated container wall, the electronic circuitry having:
  a sensor, including circuitry, for sensing a physical property or condition of the substance in operational use of the container, the sensor being positioned and contained within the laminated container wall, the laminated container wall including an opening through at least the first layer, the second layer, electrically conductive layer and the fifth layer that exposes the sensor to the space containing the substance in operational use of the container,
  a processing circuit positioned at the first side and configured and arranged with the sensor to compare a value associated with the sensed physical property or condition of the substance to a predetermined threshold value, and to generate a radio-frequency signal indicating that the perishable substance has perished based on the value of the sensed physical property or condition and the predetermined threshold value; and
  an antenna in the third layer and having a planar configuration for communicating the radio-frequency signal to a receiver, external to the container, the processing circuit being configured and arranged to drive the antenna to communicate the radio-frequency signal, the radio-frequency signal being indicative of the physical property or condition sensed, and the antenna being
    positioned between the second side and the electrically conductive layer, and being within the laminated container wall and on a substrate that accommodates the sensor; and
  electrically isolated from the electrically conductive layer; and
  wherein the antenna is connected to the sensor circuitry via the electrically conductive connection and wherein the antenna and sensor circuit are arranged along the laminated container wall and in different planes running along the first and second sides of the laminated container wall; and
  wherein the electronic circuitry is configured and arranged to receive a wireless power signal via the antenna and to use the received wireless power signal to provide and use current for sensing the physical property or condition of the substance and for communicating the RF signal.

3. The apparatus of claim 1, wherein the sensor circuit is positioned within the laminated container wall, the laminated wall further including an opening through at least the electrically conductive layer that exposes the sensor circuit to the space configured and arranged to contain the substance;
  the electronic circuitry includes processing circuitry positioned at the inner side and connected to the sensor, and a connecting circuit that connects the processing circuitry to the antenna through another opening, that is insulated, in the electrically conductive layer, wherein the insulated opening is filled with an electrically insulating material configured and arranged to mitigate galvanic contact between the electrically conductive layer and the connecting circuit; and
  the processing circuitry is configured and arranged with the sensor to
    process signals received from the sensor and indicative of the sensed physical property or condition, and generate an RF signal based upon the processed signals, and communicate the RF signal by passing the RF signal to the antenna via the connecting circuit.

4. The apparatus of claim 3, wherein the processing circuitry and the sensor circuit are part of an RFID chip and the processing circuitry is configured and arranged with the sensor to communicate RF signals indicative of an identification of the RFID chip, by driving the antenna via the connecting circuit, and wherein the electrically conductive layer at least partially surrounds the space to reduce exposure to light or oxygen in the space.

5. The apparatus of claim 4, wherein the RFID chip includes a battery that powers the sensor circuit and the processing circuit, and wherein the processing circuit is further configured and arranged to:
  activate the sensor circuit in response to receiving a radio frequency signal from the receiver, and
  transmit the radio-frequency signal indicative of the physical property or condition sensed by the sensor circuit to the receiver, after activating the sensor circuit.

6. The apparatus of claim 4, wherein the RFID chip is configured and arranged to receive a wireless power signal via the antenna and the connecting circuit, and to use the received wireless power signal to provide current that powers the sensor circuit and the processing circuitry.

7. The apparatus of claim 3, wherein the electronic circuitry includes a memory circuit configured and arranged to store sensor data corresponding to the sensed physical property or condition of the substance, and the processing circuitry is configured and arranged with the sensor circuit to access the sensor data in the memory circuit and generate the RF signal based on the accessed sensor data.

8. The apparatus of claim 3, further including an insulating material at the insulated opening and being configured and arranged to prevent galvanic contact between the connecting circuit and the electrically conductive layer at the insulated opening.

9. The apparatus of claim 1, wherein the antenna is in contact with the outer side of the laminated container wall and is substantially parallel with the outer side of the laminated container wall and wherein the sensor circuit is arranged in or on the fifth layer and the antenna is arranged in the third layer, and wherein the antenna is connected to the sensor circuit via an electrically conductive connection that runs through the fourth layer and the third layer to the third layer.

10. An apparatus comprising:
  a laminated container wall that defines a space that is configured and arranged to contain a substance, the laminated container wall having an inner side and an outer side and an electrically conductive layer extending between the inner side and the outer side of the laminated container wall, the inner side facing the space and including a first layer configured and arranged to seal the substance in the inner side of the laminated container wall and a second layer arranged between the first layer and electrically conductive layer, the second layer being configured and arranged to adhere the first layer to the electrically conducting layer, the outside side including:
    a third layer configured and arranged to protect against elements from outside the container,
    a fourth layer configured and arranged to provide mechanical strength, and
    a fifth layer arranged between the fourth layer and the electrically conductive layer;

an antenna positioned between the outer side and the electrically conductive layer and arranged on a surface of a substrate in the fourth layer, the antenna being electrically isolated from the electrically conductive layer; and an integrated circuit arranged in the fifth layer and in the substrate, facing the space at the inner side and being connected to the antenna via an electrical connector that is electrically isolated from the electrically conductive layer, the integrated circuit being positioned within the laminated container wall, the laminated container wall further including an opening through at least the electrically conductive layer that exposes the integrated circuit to the space configured and arranged to contain the substance, the integrated circuit including:

a sensor configured and arranged to sense a characteristic of the substance, a memory circuit configured and arranged to store sensor data corresponding to the sensed characteristic, and processing circuitry configured and arranged to process signals received from the sensor and indicative of the sensed characteristic, generate an RF signal based upon the processed signals, and drive the antenna to communicate the RF signal, the integrated circuit being configured and arranged to sense a characteristic of the substance and to compare a value associated with the sensed characteristic of the substance to a predetermined threshold value, and configured and arranged with the antenna to access and use the stored data in the memory circuit to generate and communicate a radio-frequency (RF) signal including data specifying the value of the sensed characteristic of the substance to a receiver that is external to the container in response to the comparison of the value with the predetermined threshold value, wherein the antenna and the integrated circuit are arranged along the laminated container wall and in different planes running along the inner and outer sides of the laminated container wall.

11. The apparatus of claim 10,
wherein the integrated circuit is positioned along a surface of the inner side of the laminated container wall and is separated from the electrically conductive layer by an insulating portion of the laminated container wall,
wherein the electrical connector extends through another opening in the electrically conductive layer,
further including an insulating material at the other opening and configured and arranged to electrically isolate the electrical connector from the electrically conductive layer, and
wherein the integrated circuit is arranged in a substrate and the antenna is arranged on a surface of the substrate.

12. The apparatus of claim 10, wherein the integrated circuit is arranged in a layer of the outer side of the laminated container wall and in a substrate, and the antenna is arranged on a surface of the substrate, and the integrated circuit is exposed to the space via the opening of at least the electrically conductive layer that defines a hole and is configured and arranged with the electrically conductive layer to mitigate the passage of material between the space and an atmosphere external to the container.

13. The apparatus of claim 12, wherein
the integrated circuit is recessed from a surface of the inner side of the container in a direction toward the outer side of the container and recessed from the space,
the inner side of the container defines a hole including the opening in the electrically conductive layer and at least one other layer of the inner side and that exposes the integrated circuit to the space, and
the integrated circuit is configured and arranged to sense the characteristic via the hole in the inner side.

14. The apparatus of claim 12, wherein the integrated circuit includes:
a sensor configured and arranged to sense the characteristic of the substance; and
processing circuitry configured and arranged to process signals received from the sensor and indicative of the sensed characteristic, generate an RF signal based upon the processed signals, and drive the antenna to communicate the RF signal, and wherein the hole is defined by an opening in the electrically conductive layer and at least one other layer of the laminated container wall configured and arranged to seal the substance in the inner side of the laminated container wall.

15. The apparatus of claim 10, wherein the integrated circuit is configured and arranged to receive a wireless power signal via the antenna and to use the received wireless power signal to provide current that powers the integrated circuit for sensing the characteristic of the substance and for communicating the RF signal, and
wherein the first layer, the second layer, the electrically conductive layer, and the fifth layer are configured and arranged to define a hole exposing the sensor to the space.

16. The apparatus of claim 9, further comprising a memory circuit configured and arranged with the electronic circuitry to store a log of the sensed physical property or condition of the substance over time, and wherein the electronic circuitry is configured and arranged with the sensor circuit to:
activate the sensor circuit in response to receiving a first radio frequency control signal via the antenna,
sense the physical property or condition of the substance and store the sensed physical property or condition as the log in the memory, and
in response to receiving a second radio frequency control signal and based on the comparison, drive the antenna to communicate the radio-frequency signal, wherein the fourth and third layer are configured and arranged to define a hole filled with an electrically conductive material and the electrically conductive connection is arranged through the hole in the fourth and third layer.

17. The apparatus of claim 2, wherein the processing circuit is further configured and arranged to generate a radio-frequency signal indicating that the perishable substance has perished, based on the value associated with the sensed physical property or condition of the substance and the predetermined threshold value.

* * * * *